United States Patent

Wade et al.

[11] 4,022,765
[45] May 10, 1977

[54] TRIAZOLO[4,3-d][1,4]BENZODIAZEPINE-6-ONES

[75] Inventors: Peter C. Wade, Pennington, N.J.; B. Richard Vogt, Yardley, Pa.

[73] Assignee: E. R. Squibb & Sons, Inc., Princeton, N.J.

[22] Filed: Jan. 6, 1975

[21] Appl. No.: 538,975

[52] U.S. Cl. .................. 260/239.3 T; 424/269
[51] Int. Cl.[2] ............ C07D 471/14; C07D 401/14; C07D 413/06
[58] Field of Search .................. 260/239.3 T

[56] References Cited
UNITED STATES PATENTS

| 3,869,450 | 3/1975 | Kathawala | 260/239.3 T |
| 3,894,011 | 7/1975 | Vogt et al. | 260/239.3 T |
| 3,895,005 | 7/1975 | Vogt et al. | 260/239.3 T |

Primary Examiner—Henry R. Jiles
Assistant Examiner—Robert T. Bond
Attorney, Agent, or Firm—Lawrence S. Levinson; Merle J. Smith; Donald J. Barrack

[57] ABSTRACT

Compounds having the structure

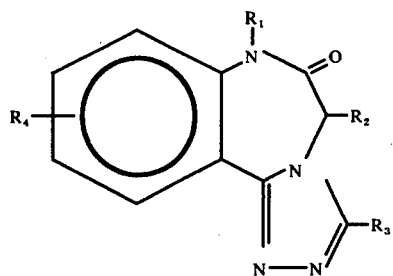

wherein $R_1$ is hydrogen, alkyl, phenyl, or benzyl; $R_2$ is hydrogen or alkyl; $R_3$ is hydrogen, alkyl, haloalkyl, cyanoalkyl, trifluoromethyl, phenyl, benzyl,

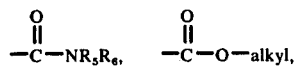

or $-(CH_2)_n-NR_5R_6$; $R_4$ is hydrogen, halogen, nitro, cyano, trifluoromethyl, alkyl, alkoxy, or alkylthio; $R_5$ and $R_6$ are the same or different and are hydrogen or alkyl or $R_5$ and $R_6$ together with the nitrogen atom to which they are attached form a five or six membered heterocyclic ring; and $n$ is 1, 2, 3 or 4; are useful as anti-inflammatory agents.

24 Claims, No Drawings

TRIAZOLO[4,3-d][1,4]BENZODIAZEPINE-6-ONES

SUMMARY OF THE INVENTION

Compounds having the structure

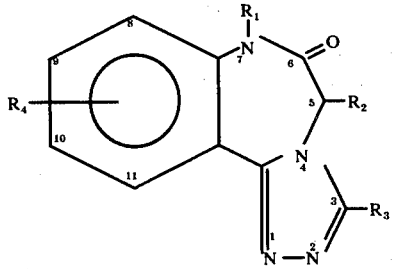

and the pharmaceutically acceptable salts thereof, are useful as anti-inflammatory agents. In formula I, and throughout the specification, the symbols have the following meaning:

$R_1$ can be hydrogen, alkyl, phenyl, or benzyl;

$R_2$ can be hydrogen or alkyl;

$R_3$ can be hydrogen, alkyl, haloalkyl, cyanoalkyl trifluoromethyl, phenyl, benzyl,

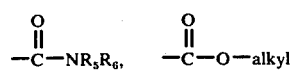

$-(CH_2)_n-NR_5R_6$;

$R_4$ can be hydrogen, halogen, nitro, cyano, trifluoromethyl, alkyl, alkoxy, or alkylthio;

$R_5$ and $R_6$ can be the same or different and can be hydrogen or alkyl, or $R_5$ and $R_6$ together with the nitrogen atom to which they are attached can form a heterocyclic ring having the formula

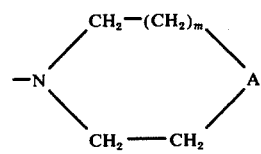

wherein $m$ is 0 or 1, A is CH—Q, N—Q, or oxygen and Q is hydrogen or alkyl, provided that when $m$ is 0, A is CH—Q; and $n$ is 1, 2, 3, or 4.

The term alkyl, as used throughout the specification, either by itself or as part of a larger group, refers to both straight and branched chain alkyl groups containing 1, 2, 3, or 4 carbon atoms.

The term "alkoxy", as used throughout the specification, refers to a group of the formula Y-O-, wherein Y is alkyl as defined above.

The term halogen, as used throughout the specification, refers to fluorine, chlorine, bromine, and iodine.

Exemplary of the heterocyclic moieties contemplated by the formula

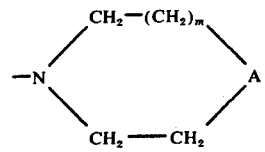

are 1-pyrrolidinyl, 1-piperidinyl, 4-morpholinyl, 1-piperazinyl, 4-alkyl-1-piperazinyl, 4-alkyl-1-piperidinyl, and 3-alkyl-1-pyrrolidinyl.

DETAILED DESCRIPTION OF THE INVENTION

The novel compounds of this invention are prepared from compounds having the formula

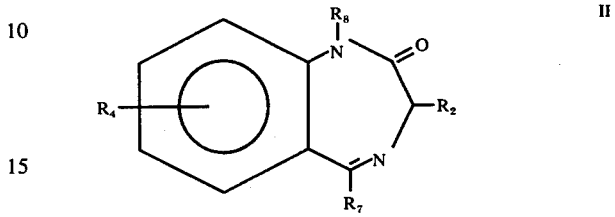

wherein $R_7$ can be halogen (preferably bromine or chlorine), sulfhydryl, alkoxy, alkylthio, or phenylalkylthio and $R_8$ can be alkyl, phenyl, or benzyl. The compounds of formula II are known; see for example U.S. Pat. No. 3,414,563 and Swiss Pat. No. 485,742.

Reaction of a benzodiazepine of formula II with an acyl hydrazine having the structure

yields a compound having the structure

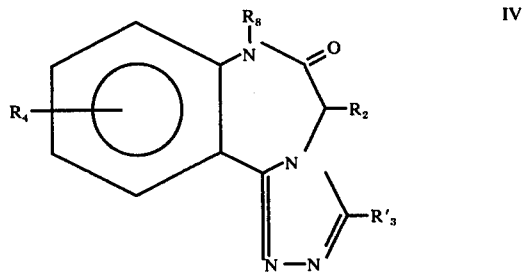

In formula III and IV, and throughout the specification, the symbols $R'_3$ can be hydrogen, alkyl, cyanoalkyl, phenyl, benzyl or

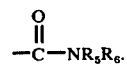

The above reaction can be run in an organic solvent at elevated temperatures, e.g., in benzene under reflux conditions.

Those compounds of formula I wherein $R_3$ is haloalkyl, trifluoromethyl, or

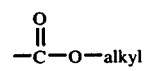

this subgrouping is hereinafter referred to as $R''_3$) can be prepared by first reacting a benzodiazepine of formula II with an alkyl carbazate

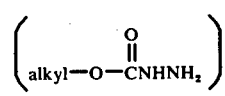

to obtain a compound having the structure

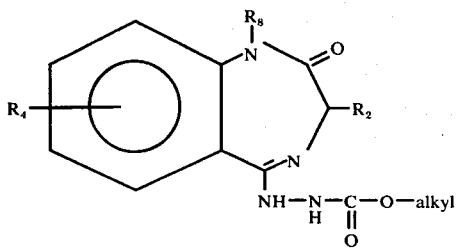
V

The preferred alkyl carbazate is t-butyl carbazate. The reaction can be run neat, or in a non-reacting organic solvent at a temperature of from about 50° C to 250° C for about 5 minutes to 24 hours, preferably from about 80° C to 140° C for about 30 minutes to 6 hours.

Reaction of a compound of formula V with either an ester of the formula

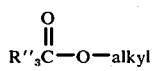
VI or an anhydride of the formula $(R''_3CO)_2O$  VII yields a compound having the structure

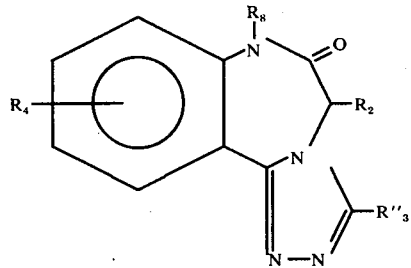
VIII

The reaction is run in the presence of an acid having the structure

IX or with a mineral acid such as hydrochloric acid, at an elevated temperature, i.e., about 50° C to 200° C. Alternatively, a compound of formula V can be pretreated with an acid and then reacted with a compound of formula VI or VII.

Compounds of formula I wherein $R_3$ is $-(CH_2-)_n-NR_5R_6$ are prepared from the corresponding compound of formula VIII wherein $R''_3$ is haloalkyl, by reaction with a compound having the formula $H-NR_5R_6$  X The reaction is run in an organic solvent, such as 1,2-dimethoxyethane, at a temperature of from 50° C to 200° C, and yields a compound having the structure

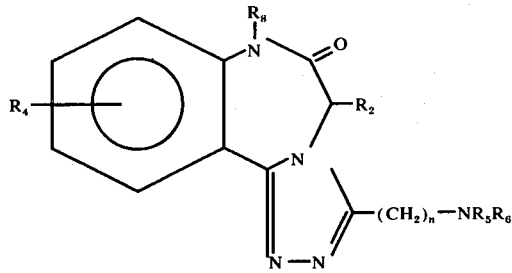
XI

Compounds of formula I wherein $R_1$ is hydrogen can be prepared by reducing the corresponding 7-benzyl derivatives of formula IV, VIII, or XI. The reduction can be carried out by reacting the compound with hydrogen under pressure in the presence of a catalyst, e.g., palladium or Raney nickel, or by reacting the compound with anhydrous, liquid hydrofluoric acid.

Compounds of formula I wherein $R_1$ is alkyl are preferred and those wherein $R_1$ is methyl are most preferred.

Compounds of formula I wherein $R_2$ is hydrogen are preferred.

Compounds of formula I wherein $R_4$ is in the 9 or 10-position of the triazolo[4,3-d][1,4]benzodiazepine nucleus are preferred.

Compounds of formula I wherein $R_4$ is halogen are preferred, and those wherein $R_4$ is chlorine are most preferred.

The triazolobenzodiazepines of formula I that contain a basic amino group can be converted into pharmaceutically acceptable acid-addition salts using procedures well known in the art. Illustrative acid-addition salts are the hydrohalides, especially the hydrochloride and hydrobromide which are preferred, sulfate, nitrate, phosphate, tartrate, maleate, fumarate, citrate, succinate, methanesulfonate, benzenesulfonate, toluenesulfonate, and the like.

The triazolobenzodiazepines of formula I, and the pharmaceutically acceptable acid-addition salts of the compound, are useful in treating inflammation in mammalian species, e.g., rats, dogs, cats, monkeys, etc. Joint tenderness and stiffness (in conditions such as rheumatoid arthritis) can be treated with the above described compounds.

The compounds of this invention can be formulated for use as anti-inflammatory agents according to accepted pharmaceutical practice in oral dosage forms such as tablets, capsules, elixirs, or powders, or in an injectable form in a sterile aqueous vehicle prepared according to conventional pharmaceutical practice. The compounds of this invention may be administered in amounts of 100 mg/70 kg/day to 2 g/70 kg/day, preferably 100 mg/70 kg/day to 1 g/70 kg/day.

Those compounds of formula I wherein $R_3$ is

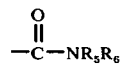

have useful central nervous system activity (in addition to their anti-inflammatory activity) and can be used as anxiolytic agents.

The following examples are specific embodiments of this invention.

EXAMPLE 1

10-Chloro-3,7-dimethyl-5H-s-triazolo[4,3-d][1,4]benzodiazepin-6(7H)-one 5,7-Dichloro-1-methyl-1,4-benzodiazepinone-2 (4.86 g) and acethydrazide (5.02 g) are refluxed together for 14 hours in benzene (300 ml). The solvent is stripped off and the residue is dissolved in hot water. On cooling, 4.2 g of white needles precipitates and are filtered off. They are recrystallized from water containing about 25% methanol. The needles are dried at 150° C under vacuum overnight. The drying process yields the title compound as a powder, melting point 228.5°–229.5° C.

EXAMPLE 2

10-Chloro-7-methyl-3-phenyl-5H-s-triazolo[4,3-d][1,4]benzodiazepin-6(7H)-one 5,7-Dichloro-1-methyl-1,4-benzodiazepinone-2 (2.79 g) and benzoylhydrazide (2.86 g) are refluxed in 150 ml of benzene for 3 hours. The solid material is filtered from the hot reaction mixture and the solvent removed from the filtrate under vacuum. The residue is recrystallized twice from methanol and dried at 125° C under vacuum for 3 hours to yield 2.9 g of the title compound, melting point 204.5°–205.5° C.

EXAMPLE 3

10-Chloro-7-methyl-5H-s-triazolo[4,3-d][1,4]benzodiazepin-6(7H)-one 5,7-Dichloro-1-methyl-1,4-benzodiazepinone-2 (14.6 g) and formylhydrazide (12 g) are refluxed in 300 ml of benzene for 3 hours. The solvent is decanted from the resulting precipitate which is recrystallized twice from 95% ethanol to yield 7.5 g of the title compound. An additional 5 g of the title compound can be obtained from the decanted solvent. The title compound has a melting point of 272°–274° C.

EXAMPLE 4

3-Acetonitrile-10-chloro-7-methyl-5H-s-triazolo[4,3-d][1,4]benzodiazepin-6(7H)-one 5,7-Dichloro-1-methyl-1,4-benzodiazepinone-2 (5 g) and cyanoacetohydrazide (3 g) are refluxed together in 150 ml of 1,2-dimethoxyethane for 5 hours. The solvent is stripped off and the residue is stirred in 95% ethanol. The ethanol is decanted and the residue (4.7 g) is recrystallized from a large volume of methanol followed by drying overnight at 100° C under vacuum to yield the title compound, melting point 252°–253.5° C.

EXAMPLE 5

3-Carboxamide-10-chloro-7-methyl-5H-s-triazolo[4,3-d][1,4]benzodiazepin-6(7H)-one 5,7-Dichloro-1-methyl-1,4-benzodiazepinone-2 (10 g) and oxamic hydrazide are refluxed for 50 minutes in 300 ml of dimethylformamide. The resulting solution is concentrated to ⅓ its original volume and allowed to stand overnight at 25° C. The resulting precipitate is filtered off and is recrystallized from dimethylformamide to give 2.7 g of a powder. An additional 5 g of material is recrystallized from the various filtrates. Drying the material overnight at 120° C under vacuum yields the title compound, melting point 303°–304° C.

EXAMPLE 6

10-Chloro-7-methyl-3-(trifluoromethyl)-5H-s-triazolo[4,3-d][1,4]benzodiazepin-6(7H)-one 5,7-Dichloro-1-methyl-1,4-benzodiazepinone-2 (7.5 g) and t-butylcarbazate (7.9 g) are refluxed in 300 ml of benzene for 90 minutes. The solvent is removed under vacuum and 20 ml of trifluoroacetic acid is added. The mixture is stirred at room temperature for 30 minutes. The trifluoroacetic acid is removed under vacuum and 30 ml of trifluoroacetic anhydride are added. The resulting solution is refluxed for 2 hours followed by evaporation of the volatiles. The residues is stirred with 250 ml of ether to yield 6.9 g of a fine powder which after recrystallization from methanol and drying under vacuum at 130° C for 3 hours, has a melting point 186°–187° C.

EXAMPLE 7

10-Chloro-6,7-dihydro-7-methyl-6-oxo-5H-s-triazolo[4,3-d][1,4]benzodiazepin-3-carboxylic acid, ethyl ester 5,7-Dichloro-1-methyl-1,4-benzodiazepinone-2 (10 g) and t-butylcarbazate (5.8 g) are refluxed in 300 ml of benzene for 5 hours. The solvent is stripped off and 5 g of oxalic acid and 30 ml of diethyl oxalate are added to the residue. The resulting solution is heated on a steam bath for 2 hours, cooled to room temperature and poured into 400 ml of ether; a precipitate forms immediately. The ether solution is decanted from the precipitate and the solvent is stripped off. The diethyl oxalate is disstilled off under vacuum and the residue is poured into 100 ml of water. The slow forming precipitate is filtered off after an hour to yield 2.5 g of material. Recrystallization from absolute ethanol yields the title compound, melting point 201°–202° C.

EXAMPLE 8

10-Chloro-7-methyl-3-(morpholinocarbonyl)-5H-s-triazolo[4,3-d][1,4]benzodiazepin-6(7H)-one 5,7-Dichloro-1-methyl-1,4-benzodiazepinone-2 (20 g) and 4-morpholineglyoxylic acid, hydrazine (15 g) are mixed together in 300 ml of dimethylformamide for 30 minutes while heating at 100° C. The solvent is stripped off and 400 ml of absolute ethanol is added to the residue. A precipate forms and the mixture is stirred overnight. The precipitate is filtered off (saving the filtrate) and stirred overnight with 400 ml of chloroform. The solid material is filtered off and the two filtrate combined. The solvents are removed under vacuum and the residue is recrystallized from absolute ethanol to yield 1.4 g of the title compound, melting point 200.5°–201.0° C.

EXAMPLE 9

10-Chloro-3-(chloromethyl)-7-methyl-5H-s-triazolo[4,3-d][1,4]benzodiazepin-6(7H)-one 5,7-Dichloro-1-methyl-1,4-benzodiazepinone-2 (2.43 g) and t-butylcarbazate (2.64 g) are refluxed in 125 ml of benzene for 90 minutes. The solvent is removed under vacuum and 9 g of chloroacetic acid is added to the residue. After heating the mixture at 80° C for 45 minutes. 7.5 g of chloroacetic anhydride is added and heating is continued at 90° C for an additional 3 hours. The mixture is crystallized from water to give 1.5 g of a solid which is dried overnight at 110° C under vacuum to yield the title compound, melting point 193°–194.5° C.

EXAMPLE 10

10-Chloro-7-methyl-3-(1-pyrrolidinylmethyl)-5H-s-triazolo[4,3-d][1,4]benzodiazepin-6(7H)-one, hydrochloride (1:1)

10-Chloro-3-(chloromethyl)-7-methyl-5H-s-triazolo[4,3-d][1,4]benzodiazepin-6(7H)-one (5 g, prepared as described in Example 9) is suspended in 150 ml of 1,2-dimethoxyethane and the suspension is stirred at 70° C. Pyrrolidine (3.6 g in 10 ml of 1,2-dimethoxyethane) is added to the stirring suspension and heating at 70° C is continued for 3 hours. The solvent is stripped off, 3N aqueous sodium hydroxide is added to the residue and the mixture is extracted four times with benzene. The combined benzene extracts are dried over sodium sulfate and decanted from the drying agent. The solvent is removed under vacuum to yield 4.4 g of a gum. The gum is dissolved in a small amount of benzene and chromatographed on an 8 × 4.25 cm column of alumina (Activity I). Benzene (700 ml) is passed through the column and discarded. The free base of the title compound is eluted with 600 ml of chloroformethyl acetate (3:2) and the solvents are removed under vacuum. The free base is taken up in a small volume of methanol and neutralized with one equivalent of ethereal hydrochloric acid. The hydrochloride is precipitated by the addition of ether, filtered, recrystallized from isopropanol and dried at 50° C under vacuum to yield 3.6 g of the title compound, melting point 238°–240° C, dec.

EXAMPLE 11

10-Chloro-7-methyl-3-(4-methyl-1-piperazinylmethyl)-5H-s-triazolo[4,3-d][1,4]benzodiazepin 6(7H)-one 10-Chloro-3-(chloromethyl)-7-methyl-5H-s-triazolo[4,3-d][1,4]benzodiazepin-6(7H)-one (5 g, prepared as described in Example 9) is suspended in 50 ml of 1,2-dimethoxyethane. N-methylpiperazine (5.4 g) is added to the suspension and the mixture is heated under reflux for 5 hours. The solvent is stripped off, 3N aqueous sodium hydroxide is added to the residue and the mixture is extracted with several portions of chloroform. The combined chloroform extracts are dried over sodium sulfate and the solvent is removed under vacuum to leave a residue which is recrystallized from absolute ethanol to yield 4 g of the title compound, melting point 228.5°–230.5° C.

EXAMPLE 12

10-Chloro-7-methyl-3-(4-methyl-1-piperazinylmethyl)-5H-s-triazol[4,3-d][1,4]benzodiazepin-6(7H)-one, hydrochloride (1:1)

10-Chloro-7-methyl-3-(4-methyl-1-piperazinylmethyl)5H-s-triazolo[4,3-d][1,4]benzodiazepin-6(7H)-one (4 g) in methanol is neutralized with 2 equivalents of ethereal hydrochloric acid and the hydrochloride is precipitated with ether. After recrystallization from absolute ethanol, the salt is allowed to stand exposed to the moist atmosphere for 7 days, finally giving the dihydrochloride sesquihydrate, melting point 235°–237° C.

EXAMPLE 13 – 22

Following the procedure of Example 1, but substituting the compound listed in column I for 5,7-dichloro-1-methyl-1,4-benzodiazepinone-2, and the compound listed in column II for acethydrazine, the compound listed in column III is obtained.

| Example | Column I | Column II | Column III |
|---|---|---|---|
| 13 | 5-chloro-1-benzyl-7-(trifluoromethyl)-1,4-benzodiazepinone-2 | phenyl acetic hydrazide | 3,7-dibenzyl-10-(trifluoromethyl)-5H-s-triazolo[4,3-d]-[1,4]benzodiazepin-6(7H)-one |
| 14 | 5-chloro-1-methyl-7-nitro-1,4-benzodiazepinone-2 | butyric hydrazide | 7-methyl-10-nitro-3-propyl-5H-s-triazolo[4,3-d][1,4]-benzodiazepin-6(7H)-one |
| 15 | 5-chloro-7-(ethylthio)-1-methyl-1,4-benzodiazepinone | valeric hydrazide | 3-butyl-10-(ethylthio)-7-methyl-5H-s-triazolo[4,3-d][1,4]benzodiazepin-6(7H)-one |
| 16 | 5-chloro-1,7-dimethyl-1,4-benzodiazepinone-2 | cyano butyric hydrazide | 3-(3-cyanopropyl)-7,10-dimethyl-5H-s-triazolo[4,3-d][1,4]benzodiazepin-6(7H)-one |
| 17 | 5-chloro-1,3-dimethyl-7-(trifluoromethyl)-1,4-benzodiazepinone-2 | acethydrazide | 3,5,7-trimethyl-10-(trifluoromethyl)-5H-s-triazolo[4,3-d]-[1,4]benzodiazepin-6(7H)-one |
| 18 | 8-bromo-5-ethoxy-1-phenyl-1,4-benzodiazepinone-2 | acethydrazide | 9-bromo-3-methyl-7-phenyl-5H-s-triazolo[4,3-d][1,4]benzodiazepin-6(7H)-one |
| 19 | 7-cyano-1-benzyl-5-(methylthio)-1,4-benzodiazepinone-2 | acethydrazide | 7-benzyl-10-cyano-3-methyl-5H-s-triazolo[4,3-d][1,4]benzodiazepin-6(7H)-one |
| 20 | 1-benzyl-1,4-benzodiazepin-2-one-5-thione | acethydrazide | 7-benzyl-3-methyl-5H-s-triazolo-[4,3-d][1,4]benzodiazepin-6(7H)-one |
| 21 | 5-chloro-1-phenyl-7-ethyl-1,4-benzodiazepinone-2 | acethydrazide | 10-ethyl-3-methyl-7-phenyl-5H-s-triazolo[4,3-d][1,4]benzodiazepin-6(7H)-one |
| 22 | 5-chloro-7-methoxy-1-methyl-1,4-benzodiazepinone-2 | acethydrazide | 10-methoxy-3,7-dimethyl-5H-s-triazolo[4,3-d]]1,4]benzodiazepin-6(7H)-one |

EXAMPLES 23 – 26

Following the procedure of Example 8, but substituting the compounds listed in column I for 4-morpholineglyoxylic acid, hydrazide, the compounds listed in column II are obtained.

| Example | Column I | column II |
|---|---|---|
| 23 | diethylaminoglyoxylic acid | 10-chloro-3-(diethylaminocarbonyl)-7- |

-continued

| Example | Column I | column II |
|---|---|---|
| | hydrazide | methyl-5H-s-triazolo[4,3-d][1,4]benzo-diazepin-6(7H)-one |
| 24 | (4-methyl-1-piperidinyl)-glyoxylic acid hydrazide | 10-chloro-7-methyl-3-(4-methyl-1-piperidinylcarbonyl)-5H-s-triazolo-[4,3-d][1,4]benzodiazepin-6(7H)-one |
| 25 | (4-(butyl-1-piperazinyl)-glyoxylic acid hydrazide | 3-(4-butyl-1-piperazinylcarbonyl)-10-chloro-7-methyl-5H-s-triazolo[4,3-d]-[1,4]benzodiazepin-6(7H)-one |
| 26 | 1-pyrrolidinylglyoxylic acid hydrazide | 10-chloro-7-methyl-3-(1-pyrrolidinyl-carbonyl)-5H-s-triazolo[4,3-d[[1,4]-benzodiazepin-6(7H)-one |

EXAMPLES 27 – 29

Following the procedure of Example 9, but substituting the compound listed in column I for chloroacetic acid, and adding one equivalent of anhydrous hydrogen chloride, the compound listed in column II is obtained.

| Example | Column I | Column II |
|---|---|---|
| 27 | 5-bromovaleric acid | 3-(4-bromobutyl)-10-chloro-7-methyl-5H-s-triazolo[4,3-d][1,4 benzodiazepin-6(7H)-one |
| 28 | 4-chlorobutyric acid | 10-chloro-3-(3-chloropropyl)-7-methyl-5H-s-triazolo[4,3-d][1,4]benzodiazepin-6(7H)-one |
| 29 | 3-chloropropionic acid | 10-chloro-3-(2-chloroethyl)-7-methyl-5H-s-triazolo[4,3-d][1,4]benzodiazepin-6(7H)-one |

EXAMPLES 30 – 32

Following the procedure of Example 11, but substituting the compound listed in column I for 10chloro3-(chloromethyl)-7-methyl-5H-s-triazolo[4,3-d][1,4]benzodiazepin-6(7H)-one and the compound listed in column II for N-methylpiperazine, the compound listed in column III is obtained.

| Example | Column I | Column II | Column III |
|---|---|---|---|
| 30 | 3-(4-bromobutyl)-10-chloro-7-methyl-5H-s-triazolo[4,3-d]-[1,4]benzodiazepin-6(7H)-one | piperidine | 10-chloro-7-methyl-3-[4-(1-piperidinyl)butyl]-5H-s-triazolo[4,3-d]-[1,4]benzodiazepin-6(7H)-one |
| 31 | 10-chloro-3-(3-chloropropyl)-7-methyl-5H-s-triazolo[4,3-d]-[1,4]benzodiazepin-6(7H)-one | 4-methyl-piperidine | 10-chloro-7-methyl-3-[3-(4-methyl-1-piperidinyl)propyl]-5H-s-triazolo-[4,3-d][1,4]benzodiazepin-6(7H)-one |
| 32 | 10-chloro-3-(2-chloroethyl)-7-methyl-5H-s-triazolo[4,3-d]-[1,4]benzodiazepin-6(7H)-one | morpholine | 10-chloro-7-methyl-3-[2-(1-morpholinyl)ethyl]-5H-s-triazolo[4,3-d]-[1,4]benzodiazepin-6(7H)-one |

EXAMPLE 33

10-chloro-3-methyl-5H-s-triazolo[4,3-d][1,4]benzodiazepin-6(7H)-one

7-Benzyl-10-chloro-3-methyl-5H-s-triazolo[4,3-d][1,4]benzodiazepin-6-(7H)-one (0.01 mole) is hydrogenated at 60° C in 300 ml of acetic acid containing 0.3 g of prereduced Raney nickel. The initial hydrogen pressure is 60 p.s.i. The reduction is stopped after 0.01 mole of hydrogen is absorbed, the catalyst is filtered off, and the solvent is evaporated. The residue is stirred with water and the title compound is filtered off and dried.

What is claimed is:
1. A compound having the structure

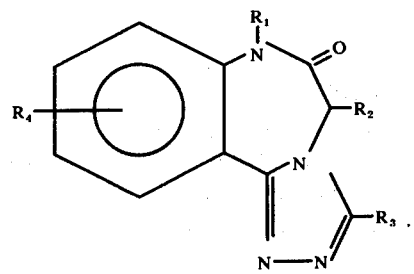

wherein $R_1$ is phenyl; $R_2$ is hydrogen or alkyl; $R_3$ is hydrogen, alkyl, haloalkyl, cyanoalkyl, trifluoromethyl, phenyl, benzyl,

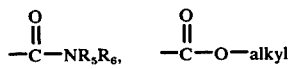

or $—(CH_2)_n—NR_5R_6$; $R_4$ is hydrogen, halogen, nitro, cyano, trifluoromethyl, alkyl, alkoxy or alkylthio; $R_5$ and $R_6$ are the same or different and are hydrogen or alkyl, or $R_5$ and $R_6$ together with the nitrogen atom to which they are attached form a heterocyclic ring having the formula

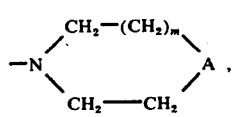

wherein $m$ is 0 or 1, A is CH—Q, N—Q or oxygen and Q is hydrogen or alkyl, provided that when $m$ is 0, A is CH—Q; and $n$ is 1, 2, 3 or 4: wherein alkyl and alkoxy in all instances refer to groups having 1 to 4 carbon atoms; and, when the compound contains a basic amino group, a pharmaceutically acceptable salt thereof.

2. A compound having the structure

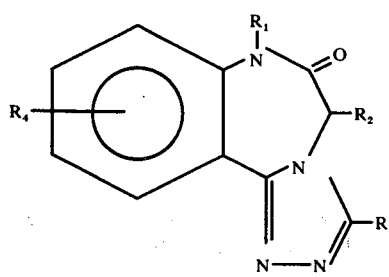

wherein $R_1$ is benzyl; $R_2$ is hydrogen or alkyl; $R_3$ is hydrogen, alkyl, haloalkyl, cyanoalkyl, trifluoromethyl, phenyl, benzyl,

or $-(CH_2)_n-NR_5R_6$; $R_4$ is hydrogen, halogen, nitro, cyano, trifluoromethyl, alkyl, alkoxy or alkylthio; $R_5$ and $R_6$ are the same or different and are hydrogen or alkyl, or $R_5$ and $R_6$ together with the nitrogen atom to which they are attached form a heterocyclic ring having the formula

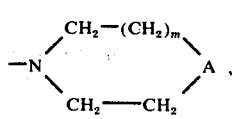

wherein $m$ is 0 or 1, A is CH—Q, N—Q or oxygen and Q is hydrogen or alkyl, provided that when $m$ is 0, A is CH-Q; and $n$ is 1, 2, 3 or 4; wherein alkyl and alkoxy in all instances refer to groups having to 1 to 4 carbon atoms; and, when the compound contains a basic amino group, a pharmaceutically acceptable salt thereof.

3. A compound having the structure

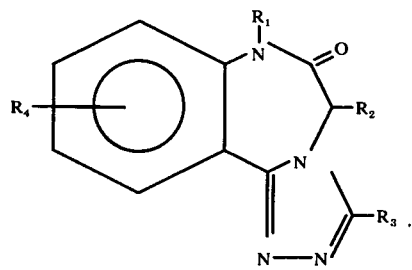

wherein $R_1$ is hydrogen, alkyl, phenyl or benzyl; $R_2$ is hydrogen or alkyl; $R_3$ is hydrogen; $R_4$ is hydrogen, halogen, nitro, cyano, trifluoromethyl, alkyl, alkoxy or alkylthio; wherein alkyl and alkoxy in all instances refer to groups having 1 to 4 carbon atoms.

4. A compound having the structure

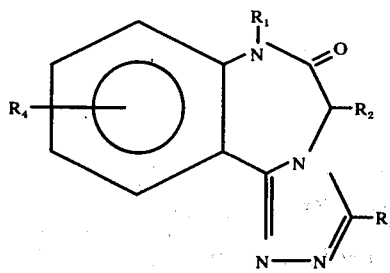

wherein $R_1$ is hydrogen, alkyl, phenyl or benzyl; $R_2$ is hydrogen or alkyl; $R_3$ is alkyl; $R_4$ is hydrogen, halogen, nitro, cyano, trifluoromethyl, alkyl, alkoxy or alkylthio; wherein alkyl and alkoxy in all instances refer to groups having 1 to 4 carbon atoms.

5. A compound having the structure

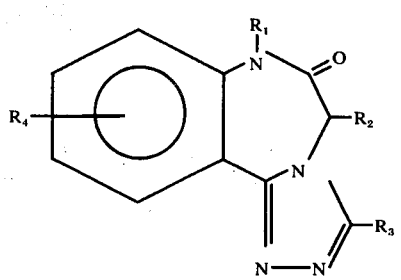

wherein $R_1$ is hydrogen, alkyl, phenyl or benzyl; $R_2$ is hydrogen or alkyl; $R_3$ is haloalkyl; $R_4$ is hydrogen, halogen, nitro, cyano, trifluoromethyl, alkyl, alkoxy or alkylthio; wherein alkyl and alkoxy in all instances refer to groups having 1 to 4 carbon atoms.

6. A compound having the structure

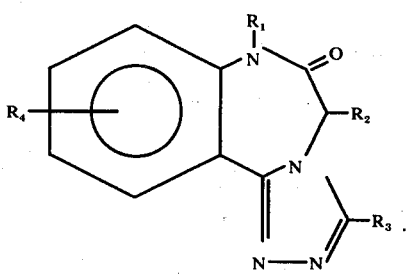

wherein $R_1$ is hydrogen, alkyl, phenyl or benzyl; $R_2$ is hydrogen or alkyl; $R_3$ is cyanoalkyl; $R_4$ is hydrogen, halogen, nitro, cyano, trifluoromethyl, alkyl, alkoxy or alkylthio; wherein alkyl and alkoxy in all instances refer to groups having 1 to 4 carbon atoms.

7. A compound having the structure

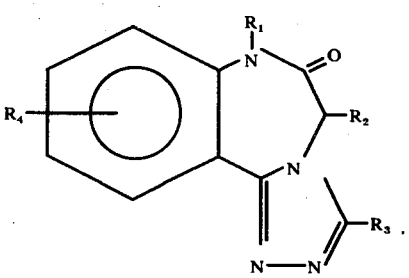

wherein $R_1$ is hydrogen, alkyl, phenyl or benzyl; $R_2$ is hydrogen or alkyl; $R_3$ is trifluoromethyl; $R_4$ is hydrogen, halogen, nitro, cyano, trifluoromethyl, alkyl, alkoxy or alkylthio; wherein alkyl and alkoxy in all instances refer to groups having 1 to 4 carbon atoms.

8. A compound having the structure

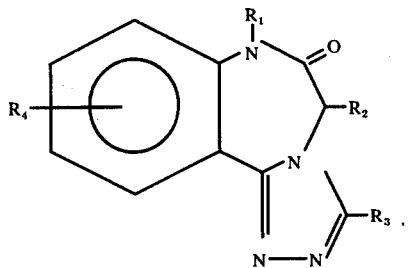

wherein $R_1$ is hydrogen, alkyl, phenyl or benzyl; $R_2$ is hydrogen or alkyl; $R_3$ is benzyl; $R_4$ is hydrogen, halogen, nitro, cyano, trifluoromethyl, alkyl, alkoxy or alkylthio; wherein alkyl and alkoxy in all instances refer to groups having 1 to 4 carbon atoms.

9. A compound having the structure

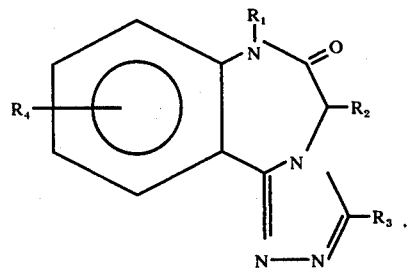

wherein $R_1$ is hydrogen, alkyl, phenyl or benzyl; $R_2$ is hydrogen or alkyl; $R_3$ is

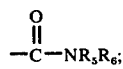

$R_4$ is hydrogen, halogen, nitro, cyano, trifluoromethyl, alkyl, alkoxy or alkylthio; $R_5$ and $R_6$ are the same or different and are hydrogen or alkyl; wherein alkyl and alkoxy in all instances refer to groups having 1 to 4 carbon atoms.

10. A compound having the structure

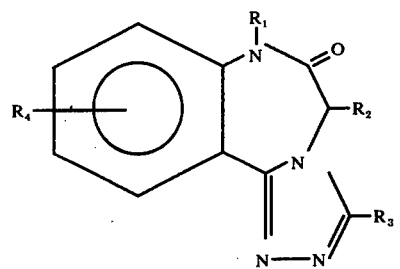

wherein $R_1$ is hydrogen, alkyl, phenyl or benzyl; $R_2$ is hydrogen or alkyl; $R_3$ is

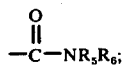

$R_4$ is hydrogen, halogen, nitro, cyano, trifluoromethyl, alkyl, alkoxy or alkylthio; $R_5$ and $R_6$ together with the nitrogen atom to which they are attached form a heterocyclic ring having the formula

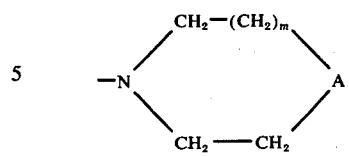

wherein $m$ is 0 or 1, A is CH-Q, N—Q or oxygen and Q is hydrogen or alkyl, provided that when m is O, A is CH-Q; wherein alkyl and alkoxy in all instances refer to groups having 1 to 4 carbon atoms.

11. A compound having the structure

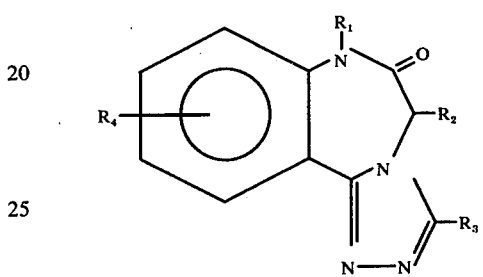

wherein $R_1$ is hydrogen, alkyl, phenyl or benzyl; $R_2$ is hydrogen or alkyl; $R_3$ is

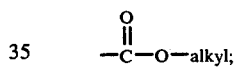

$R_4$ is hydrogen, halogen, nitro, cyano, trifluoromethyl, alkyl, alkoxy or alkylthio; wherein alkyl and alkoxy in all instances refer to groups having 1 to 4 carbon atoms.

12. A compound having the structure

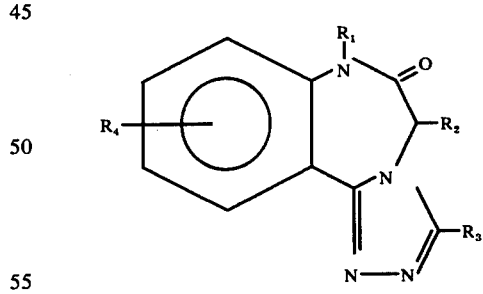

wherein $R_1$ is hydrogen, alkyl, phenyl or benzyl; $R_2$ is hydrogen or alkyl; $R_3$ is $-(CH_2)_n-NR_5R_6$; $R_4$ is hydrogen, halogen, nitro, cyano, trifluoromethyl, alkyl, alkoxy or alkylthio; $R_5$ and $R_6$ are the same or different and are hydrogen or alkyl; and $n$ is 1, 2, 3 or 4 wherein alkyl and alkoxy in all instances refer to groups having 1 to 4 carbon atoms; or a pharmaceutically acceptable salt thereof.

13. A compound having the structure

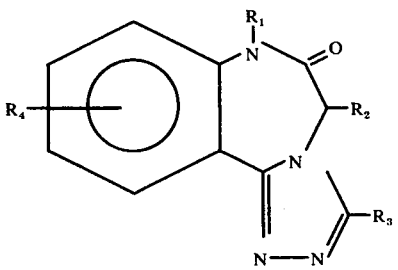

wherein $R_1$ is hydrogen, alkyl, phenyl or benzyl; $R_2$ is hydrogen or alkyl; $R_3$ is —$(CH_2)_n$—$NR_5R_6$; $R_4$ is hydrogen, halogen, nitro, cyano, trifluromethyl, alkyl, alkoxy or alkylthio; $R_5$ and $R_6$ together with the nitrogen atom to which they are attached form a heterocyclic ring having the formula

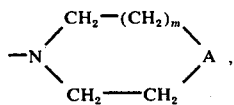

wherein $m$ is 0 or 1, A is CH—Q, N—Q or oxygen and Q is hydrogen or alkyl, provided that when $m$ is 0, A is CH-Q; and $n$ is 1, 2, 3 or 4; wherein alkyl and alkoxy in all instances refer to groups having 1 to 4 carbon atoms; or a pharmaceutically acceptable salt thereof.

14. The compound in accordance with claim 4 having the name 10-chloro-3,7-dimethyl-5H-s-triazolo[4,3-d][1,4]benzodiazepin-6(7H)-one.

15. The compound in accordance with claim 3 having the name 10-chloro-7-methyl-5H-s-triazolo[4,3-d][1,4]benzodiazepin-6(7H)-one.

16. The compound in accordance with claim 6 having the name 3-acetonitrile-10-chloro-7-methyl-5-H-s-triazolo[4,3-d][1,4]benzodiazepin-6(7H)-one.

17. The compound in accordance with claim 9 having the name 3-carboxamide-10-chloro-7-methyl-5H-s-triazolo[4,3-d][1,4]benzodiazepin-6(7H)-one.

18. The compound in accordance with claim 7 having the name 10-chloro-7-methyl-3-(trifluoromethyl)-5H-s-triazolo[4,3-d][1,4]benzodiazepin-6(7H)-one.

19. The compound in accordance with claim 11 having the name 10-chloro-6,7-dihydro-7-methyl-6-oxo-5H-s-triazolo[4,3-d][1,4]benzodiazepin-3-carboxylic acid, ethyl ester.

20. The compound in accordance with claim 10 having the name 10-chloro-7-methyl-3-(morpholinocarbonyl)-5H-s-triazolo[4,3-d][1,4]benzodiazepin-6(7H)-one.

21. The compound in accordance with claim 5 having the name 10-chloro-3-(chloromethyl)-7-methyl-5-H-s-triazolo[4,3-d][1,4]benzodiazepin-6(7H)-one.

22. The compound in accordance with claim 13 having the name 20-chloro-7-methyl-3-(1-pyrrolidinylmethyl)-5H-s-triazolo[4,3-d][1,4]benzodiazepin-6(H)-one, hydrochloride.

23. The compound in accordance with claim 13 having the name 10-chloro-7-methyl-3-(4-methyl-1-piperazinylmethyl)-5H-s-triazolo[4,3-d][1,4]benzodiazepin-6(7H)-one.

24. The compound in accordance with claim 13 having the name 10-chloro-7-methyl-3-(4-methyl-1-piperazinylmethyl)5H-s-triazolo[4,3-d][1,4]benzodiazepin-6(7H)-one, hydrochloride.

* * * * *

UNITED STATES PATENT AND TRADEMARK OFFICE
CERTIFICATE OF CORRECTION

PATENT NO. : 4,022,765
DATED : May 10, 1977
INVENTOR(S) : Peter C. Wade et al.

It is certified that error appears in the above-identified patent and that said Letters Patent are hereby corrected as shown below:

```
Column 1, line 29, please add the word "or" after
    the second formula.
Column 3, line 25, "VIII" should read -- VII --.
Column 8, line 14, "triazol" should read -- triazolo --.
Example 27, Column II-second line,"[1,4" should
    read -- [1,4] --.
Column 16, line 25, "20-chloro-" should read
    -- 10-chloro- --.
```

*Signed and Sealed this*

*Fourth* Day of *October 1977*

[SEAL]

Attest:

RUTH C. MASON
*Attesting Officer*

LUTRELLE F. PARKER
*Acting Commissioner of Patents and Trademarks*